United States Patent [19]

Lysko et al.

[11] Patent Number: 5,683,903

[45] Date of Patent: Nov. 4, 1997

[54] ATTACHMENT ENHANCED 293 CELLS

[75] Inventors: Paul G. Lysko, Downingtown; Nabil A. Elshourbagy, West Chester; Mary E. Brawner, Berwyn, all of Pa.

[73] Assignee: SmithKline Beecham Corporation, Philadelphia, Pa.

[21] Appl. No.: 453,117

[22] Filed: May 30, 1995

[51] Int. Cl.$^6$ ........................... C12N 5/00
[52] U.S. Cl. .................. 435/240.2; 435/7.2; 435/7.1; 435/252.3; 435/320.1; 435/65.1; 435/70.1; 435/70.3; 435/240.23; 536/23.5; 530/350; 530/395
[58] Field of Search ...................... 530/350, 395; 536/23.5; 435/7.1, 7.2, 240.2, 252.3, 320.1, 69.1, 70.1, 70.3, 240.23

[56] References Cited

U.S. PATENT DOCUMENTS 5,510,466 4/1996 Krieger et al. .................. 530/395

FOREIGN PATENT DOCUMENTS 9214482 9/1992 WIPO.

OTHER PUBLICATIONS

Sprengel et al. (1989) J. Biol. Chem. 264:20415–21.

Matsumoto et al. (1990) PNAS 87:9133–37.

Kodama et al. (1990) Nature 343:531–35.

Primary Examiner—Stephen Walsh
Assistant Examiner—Kenneth A. Sorensen
Attorney, Agent, or Firm—Edward T. Lentz; Stephen A. Venetianer; William T. King

[57] ABSTRACT

Attachment enhanced human embryonic kidney cells, 293, are provided. These cells have been modified to contain a selected mammalian scavenger gene, which has been found to improve the ability of these cells to attach in culture. The improved cells of the invention are useful in assays in which the unmodified 293 cells could be used.

12 Claims, 5 Drawing Sheets

Human Macrophage Scavenger Receptor Type I
Nucleic acid SEQ ID NO:1 and Amino Acid SEQ ID NO:2 Sequences

```
AGAGAAGTGG ATAAATCAGT GCTGCTTTCT TTAGGACGAA AGAAGT ATG GAG CAG        55
                                                  Met Glu Gln
                                                    1

TGG GAT CAC TTT CAC AAT CAA CAG GAG GAC ACT GAT AGC TGC TCC GAA      103
Trp Asp His Phe His Asn Gln Gln Glu Asp Thr Asp Ser Cys Ser Glu
      5                  10                  15

TCT GTG AAA TTT GAT GCT CGC TCA ATG ACA GCT TTG CTT CCT CCG AAT      151
Ser Val Lys Phe Asp Ala Arg Ser Met Thr Ala Leu Leu Pro Pro Asn
 20                  25                  30                  35

CCT AAA AAC AGC CCT TCC CTT CAA GAG AAA CTG AAG TCC TTC AAA GCT      199
Pro Lys Asn Ser Pro Ser Leu Gln Glu Lys Leu Lys Ser Phe Lys Ala
                  40                  45                  50

GCA CTG ATT GCC CTT TAC CTC CTC GTG TTT GCA GTT CTC ATC CCT CTC      247
Ala Leu Ile Ala Leu Tyr Leu Leu Val Phe Ala Val Leu Ile Pro Leu
                55                  60                  65

ATT GGA ATA GTG GCA GCT CAA CTC CTG AAG TGG GAA ACG AAG AAT TGC      295
Ile Gly Ile Val Ala Ala Gln Leu Leu Lys Trp Glu Thr Lys Asn Cys
              70                  75                  80

TCA GTT AGT TCA ACT AAT GCA AAT GAT ATA ACT CAA AGT CTC ACG GGA      343
Ser Val Ser Ser Thr Asn Ala Asn Asp Ile Thr Gln Ser Leu Thr Gly
         85                  90                  95

AAA GGA AAT GAC AGC GAA GAG GAA ATG AGA TTT CAA GAA GTC TTT ATG      391
Lys Gly Asn Asp Ser Glu Glu Glu Met Arg Phe Gln Glu Val Phe Met
100                 105                 110                 115

GAA CAC ATG AGC AAC ATG GAG AAG AGA ATC CAG CAT ATT TTA GAC ATG      439
Glu His Met Ser Asn Met Glu Lys Arg Ile Gln His Ile Leu Asp Met
                    120                 125                 130

GAA GCC AAC CTC ATG GAC ACA GAG CAT TTC CAA AAT TTC AGC ATG ACA      487
Glu Ala Asn Leu Met Asp Thr Glu His Phe Gln Asn Phe Ser Met Thr
                135                 140                 145

ACT GAT CAA AGA TTT AAT GAC ATT CTT CTG CAG CTA AGT ACC TTG TTT      535
Thr Asp Gln Arg Phe Asn Asp Ile Leu Leu Gln Leu Ser Thr Leu Phe
            150                 155                 160

TCC TCA GTC CAG GGA CAT GGG AAT GCA ATA GAT GAA ATC TCC AAG TCC      583
Ser Ser Val Gln Gly His Gly Asn Ala Ile Asp Glu Ile Ser Lys Ser
        165                 170                 175

TTA ATA AGT TTG AAT ACC ACA TTG CTT GAT TTG CAG CTC AAC ATA GAA      631
Leu Ile Ser Leu Asn Thr Thr Leu Leu Asp Leu Gln Leu Asn Ile Glu
180                 185                 190                 195

AAT CTG AAT GGC AAA ATC CAA GAG AAT ACC TTC AAA CAA CAA GAG GAA      679
Asn Leu Asn Gly Lys Ile Gln Glu Asn Thr Phe Lys Gln Gln Glu Glu
                    200                 205                 210

ATC AGT AAA TTA GAG GAG CGT GTT TAC AAT GTA TCA GCA GAA ATT ATG      727
Ile Ser Lys Leu Glu Glu Arg Val Tyr Asn Val Ser Ala Glu Ile Met
                215                 220                 225
```

FIG. 1A

```
GCT ATG AAA GAA GAA CAA GTG CAT TTG GAA CAG GAA ATA AAA GGA GAA        775
Ala Met Lys Glu Glu Gln Val His Leu Glu Gln Glu Ile Lys Gly Glu
        230             235             240

GTG AAA GTA CTG AAT AAC ATC ACT AAT GAT CTC AGA CTG AAA GAT TGG        823
Val Lys Val Leu Asn Asn Ile Thr Asn Asp Leu Arg Leu Lys Asp Trp
    245             250             255

GAA CAT TCT CAG ACC TTG AGA AAT ATC ACT TTA ATT CAA GGT CCT CCT        871
Glu His Ser Gln Thr Leu Arg Asn Ile Thr Leu Ile Gln Gly Pro Pro
260             265             270             275

GGA CCC CCG GGT GAA AAA GGA GAT CGA GGT CCC ACT GGA GAA AGT GGT        919
Gly Pro Pro Gly Glu Lys Gly Asp Arg Gly Pro Thr Gly Glu Ser Gly
            280             285             290

CCA CGA GGA TTT CCA GGT CCA ATA GGT CCT CCG GGT CTT AAA GGT GAT        967
Pro Arg Gly Phe Pro Gly Pro Ile Gly Pro Pro Gly Leu Lys Gly Asp
                295             300             305

CGG GGA GCA ATT GGC TTT CCT GGA AGT CGA GGA CTC CCA GGA TAT GCC       1015
Arg Gly Ala Ile Gly Phe Pro Gly Ser Arg Gly Leu Pro Gly Tyr Ala
            310             315             320

GGA AGG CCA GGA AAT TCT GGA CCA AAA GGC CAG AAA GGG GAA AAG GGG       1063
Gly Arg Pro Gly Asn Ser Gly Pro Lys Gly Gln Lys Gly Glu Lys Gly
    325             330             335

AGT GGA AAC ACA TTA ACT CCA TTT ACG AAA GTT CGA CTG GTC GGT GGG       1111
Ser Gly Asn Thr Leu Thr Pro Phe Thr Lys Val Arg Leu Val Gly Gly
340             345             350             355

AGC GGC CCT CAC GAG GGG AGA GTG GAG ATA CTC CAC AGC GGC CAG TGG       1159
Ser Gly Pro His Glu Gly Arg Val Glu Ile Leu His Ser Gly Gln Trp
            360             365             370

GGT ACA ATT TGT GAC GAT CGC TGG GAA GTG CGC GTT GGA CAG GTC GTC       1207
Gly Thr Ile Cys Asp Asp Arg Trp Glu Val Arg Val Gly Gln Val Val
                375             380             385

TGT AGG AGC TTG GGA TAC CCA GGT GTT CAA GCC GTG CAC AAG GCA GCT       1255
Cys Arg Ser Leu Gly Tyr Pro Gly Val Gln Ala Val His Lys Ala Ala
        390             395             400

CAC TTT GGA CAA GGT ACT GGT CCA ATA TGG CTG AAT GAA GTG TTT TGT       1303
His Phe Gly Gln Gly Thr Gly Pro Ile Trp Leu Asn Glu Val Phe Cys
            405             410             415

TTT GGG AGA GAA TCA TCT ATT GAA GAA TGT AAA ATT CGG CAA TGG GGG       1351
Phe Gly Arg Glu Ser Ser Ile Glu Glu Cys Lys Ile Arg Gln Trp Gly
420             425             430             435

ACA AGA GCC TGT TCA CAT TCT GAA GAT GCT GGA GTC ACT TGC ACT TTA       1399
Thr Arg Ala Cys Ser His Ser Glu Asp Ala Gly Val Thr Cys Thr Leu
            440             445             450

TAA TGCATCATAT TTTCATTCAC AACTATGAAA TCGCTGCTCA AAAATGATTT           1452

TATTACCTTG TTCCTGTAAA ATCCATTTAA TCAATATTTA AGAGATTAAG AATATTGCCC     1512

AAATAATATT TTAGATTACA GGATTAATAT ATTGAACACC TTCATGCTTA CTATTTTATG    1572
```

FIG. IB

```
TCTATATTTA AATCATTTTA ACTTCTATAG GTTTTTAAAT GGAATTTTCT AATATAATGA    1632
CTTATATGCT GAATTGAACA TTTTGAAGTT TATAGCTTCC AGATTACAAA GGCCAAGGGT    1692
AATAGAAATG CATACCAGTA ATTGGCTCCA ATTCATAATA TGTTCACCAG GAGATTACAA    1752
TTTTTTGCTC TTCTTGTCTT TGTAATCTAT TTAGTTGATT TTAATTACTT TCTGAATAAC    1812
GGAAGGGATC AGAAGATATC TTTTGTGCCT AGATTGCAAA ATCTCCAATC CACACATATT.   1872
GTTTTAAAAT AAGAATGTTA TCCAACTATT AAGATATCTC AATGTGCAAT AACTTGTGTA    1932
TTAGATATCA ATGTTAATGA TATGTCTTGG CCACTATGGA CCAGGGAGCT TATTTTTCTT    1992
GTCATGTACT GACAACTGTT TAATTGAATC ATGAAG                              2028
```

FIG. IC

Human Macrophage Scavenger Receptor Type II
Nucleic acid SEQ ID NO:3 and Amino Acid SEQ ID NO:4 Sequences

```
TAGGTTTCAA TTGTAAAGAG AGAGAAGTGG ATAAATCAGT GCTGCTTTCT TTAGGACGAA         60

AGAAGT ATG GAG CAG TGG GAT CAC TTT CAC AAT CAA CAG GAG GAC ACT          108
       Met Glu Gln Trp Asp His Phe His Asn Gln Gln Glu Asp Thr
       1             5                  10

GAT AGC TGC TCC GAA TCT GTG AAA TTT GAT GCT CGC TCA ATG ACA GCT         156
Asp Ser Cys Ser Glu Ser Val Lys Phe Asp Ala Arg Ser Met Thr Ala
15                  20                  25                  30

TTG CTT CCT CCG AAT CCT AAA AAC AGC CCT TCC CTT CAA GAG AAA CTG         204
Leu Leu Pro Pro Asn Pro Lys Asn Ser Pro Ser Leu Gln Glu Lys Leu
                35                  40                  45

AAG TCC TTC AAA GCT GCA CTG ATT GCC CTT TAC CTC CTC GTG TTT GCA         252
Lys Ser Phe Lys Ala Ala Leu Ile Ala Leu Tyr Leu Leu Val Phe Ala
            50                  55                  60

GTT CTC ATC CCT CTC ATT GGA ATA GTG GCA GCT CAA CTC CTG AAG TGG         300
Val Leu Ile Pro Leu Ile Gly Ile Val Ala Ala Gln Leu Leu Lys Trp
        65                  70                  75

GAA ACG AAG AAT TGC TCA GTT AGT TCA ACT AAT GCA AAT GAT ATA ACT         348
Glu Thr Lys Asn Cys Ser Val Ser Ser Thr Asn Ala Asn Asp Ile Thr
        80                  85                  90

CAA AGT CTC ACG GGA AAA GGA AAT GAC AGC GAA GAG GAA ATG AGA TTT         396
Gln Ser Leu Thr Gly Lys Gly Asn Asp Ser Glu Glu Glu Met Arg Phe
95                  100                 105                 110

CAA GAA GTC TTT ATG GAA CAC ATG AGC AAC ATG GAG AAG AGA ATC CAG         444
Gln Glu Val Phe Met Glu His Met Ser Asn Met Glu Lys Arg Ile Gln
                115                 120                 125

CAT ATT TTA GAC ATG GAA GCC AAC CTC ATG GAC ACA GAG CAT TTC CAA         492
His Ile Leu Asp Met Glu Ala Asn Leu Met Asp Thr Glu His Phe Gln
            130                 135                 140

AAT TTC AGC ATG ACA ACT GAT CAA AGA TTT AAT GAC ATT CTT CTG CAG         540
Asn Phe Ser Met Thr Thr Asp Gln Arg Phe Asn Asp Ile Leu Leu Gln
        145                 150                 155

CTA AGT ACC TTG TTT TCC TCA GTC CAG GGA CAT GGG AAT GCA ATA GAT         588
Leu Ser Thr Leu Phe Ser Ser Val Gln Gly His Gly Asn Ala Ile Asp
        160                 165                 170

GAA ATC TCC AAG TCC TTA ATA AGT TTG AAT ACC ACA TTG CTT GAT TTG         636
Glu Ile Ser Lys Ser Leu Ile Ser Leu Asn Thr Thr Leu Leu Asp Leu
175                 180                 185                 190

CAG CTC AAC ATA GAA AAT CTG AAT GGC AAA ATC CAA GAG AAT ACC TTC         684
Gln Leu Asn Ile Glu Asn Leu Asn Gly Lys Ile Gln Glu Asn Thr Phe
            195                 200                 205

AAA CAA CAA GAG GAA ATC AGT AAA TTA GAG GAG CGT GTT TAC AAT GTA         732
Lys Gln Gln Glu Glu Ile Ser Lys Leu Glu Glu Arg Val Tyr Asn Val
        210                 215                 220
```

FIG. 2A

```
TCA GCA GAA ATT ATG GCT ATG AAA GAA GAA CAA GTG CAT TTG GAA CAG         780
Ser Ala Glu Ile Met Ala Met Lys Glu Glu Gln Val His Leu Glu Gln
        225             230                 235

GAA ATA AAA GGA GAA GTG AAA GTA CTG AAT AAC ATC ACT AAT GAT CTC         828
Glu Ile Lys Gly Glu Val Lys Val Leu Asn Asn Ile Thr Asn Asp Leu
        240             245                 250

AGA CTG AAA GAT TGG GAA CAT TCT CAG ACC TTG AGA AAT ATC ACT TTA         876
Arg Leu Lys Asp Trp Glu His Ser Gln Thr Leu Arg Asn Ile Thr Leu
255             260                 265                 270

ATT CAA GGT CCT CCT GGA CCC CCG GGT GAA AAA GGA GAT CGA GGT CCC         924
Ile Gln Gly Pro Pro Gly Pro Pro Gly Glu Lys Gly Asp Arg Gly Pro
                275                 280                 285

ACT GGA GAA AGT GGT CCA CGA GGA TTT CCA GGT CCA ATA GGT CCT CCG         972
Thr Gly Glu Ser Gly Pro Arg Gly Phe Pro Gly Pro Ile Gly Pro Pro
        290                 295                 300

GGT CTT AAA GGT GAT CGG GGA GCA ATT GGC TTT CCT GGA AGT CGA GGA         1020
Gly Leu Lys Gly Asp Arg Gly Ala Ile Gly Phe Pro Gly Ser Arg Gly
        305                 310                 315

CTC CCA GGA TAT GCC GGA AGG CCA GGA AAT TCT GGA CCA AAA GGC CAG         1068
Leu Pro Gly Tyr Ala Gly Arg Pro Gly Asn Ser Gly Pro Lys Gly Gln
        320                 325                 330

AAA GGG GAA AAG GGG AGT GGA AAC ACA TTA AGA CCA GTA CAA CTC ACT         1116
Lys Gly Glu Lys Gly Ser Gly Asn Thr Leu Arg Pro Val Gln Leu Thr
335                 340                 345                 350

GAT CAT ATT AGG GCA GGG CCC TCT TAA GATCAGGTGG GTTGGGCGGG               1163
Asp His Ile Arg Ala Gly Pro Ser
                355

ACATCCTCTG CTACCATCTC ATTAAAAGGC CCTTCACCTC TGGACAAGTC ATCTGCAACA       1223

ACTGACTTCC AAGATCCTTT TGTGACTCCT CCAAATGACT TTGGTTCCCG TGTTGTACCT       1283

GACTTCCACA TGGCCTTCTC TCCTGGTCCC TGGTGCTGTT TGGGCCTCTG CTCCCATGCT       1343

CATACCTCTT CTTACTCCAA TTAC                                              1367
```

FIG. 2B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2028 base pairs
        ( B ) TYPE: nucleic acid
        ( C ) STRANDEDNESS: double
        ( D ) TOPOLOGY: Not Relevant ( i i ) MOLECULE TYPE: cDNA to mRNA ( i x ) FEATURE:
        ( A ) NAME/KEY: CDS
        ( B ) LOCATION: 47..1402

( x i ) SEQUENCE DESCRIPTION: SEQ ID NO:1:

```
AGAGAAGTGG ATAAATCAGT GCTGCTTTCT TTAGGACGAA AGAAGT ATG GAG CAG           55
                                                  Met Glu Gln
                                                    1

TGG GAT CAC TTT CAC AAT CAA CAG GAG GAC ACT GAT AGC TGC TCC GAA         103
Trp Asp His Phe His Asn Gln Gln Glu Asp Thr Asp Ser Cys Ser Glu
      5              10                  15

TCT GTG AAA TTT GAT GCT CGC TCA ATG ACA GCT TTG CTT CCT CCG AAT         151
Ser Val Lys Phe Asp Ala Arg Ser Met Thr Ala Leu Leu Pro Pro Asn
 20              25              30                      35

CCT AAA AAC AGC CCT TCC CTT CAA GAG AAA CTG AAG TCC TTC AAA GCT         199
Pro Lys Asn Ser Pro Ser Leu Gln Glu Lys Leu Lys Ser Phe Lys Ala
              40              45              50

GCA CTG ATT GCC CTT TAC CTC CTC GTG TTT GCA GTT CTC ATC CCT CTC         247
Ala Leu Ile Ala Leu Tyr Leu Leu Val Phe Ala Val Leu Ile Pro Leu
          55                  60                  65

ATT GGA ATA GTG GCA GCT CAA CTC CTG AAG TGG GAA ACG AAG AAT TGC         295
Ile Gly Ile Val Ala Ala Gln Leu Leu Lys Trp Glu Thr Lys Asn Cys
          70                  75                  80
```

| | | | | | | | | | | | | | | | | |
|---|---|---|---|---|---|---|---|---|---|---|---|---|---|---|---|---|
| TCA | GTT | AGT | TCA | ACT | AAT | GCA | AAT | GAT | ATA | ACT | CAA | AGT | CTC | ACG | GGA | 343 |
| Ser | Val | Ser | Ser | Thr | Asn | Ala | Asn | Asp | Ile | Thr | Gln | Ser | Leu | Thr | Gly | |
| | 85 | | | | 90 | | | | | 95 | | | | | | |
| AAA | GGA | AAT | GAC | AGC | GAA | GAG | GAA | ATG | AGA | TTT | CAA | GAA | GTC | TTT | ATG | 391 |
| Lys | Gly | Asn | Asp | Ser | Glu | Glu | Glu | Met | Arg | Phe | Gln | Glu | Val | Phe | Met | |
| 100 | | | | | 105 | | | | | 110 | | | | | 115 | |
| GAA | CAC | ATG | AGC | AAC | ATG | GAG | AAG | AGA | ATC | CAG | CAT | ATT | TTA | GAC | ATG | 439 |
| Glu | His | Met | Ser | Asn | Met | Glu | Lys | Arg | Ile | Gln | His | Ile | Leu | Asp | Met | |
| | | | 120 | | | | | 125 | | | | | 130 | | | |
| GAA | GCC | AAC | CTC | ATG | GAC | ACA | GAG | CAT | TTC | CAA | AAT | TTC | AGC | ATG | ACA | 487 |
| Glu | Ala | Asn | Leu | Met | Asp | Thr | Glu | His | Phe | Gln | Asn | Phe | Ser | Met | Thr | |
| | | | 135 | | | | 140 | | | | | 145 | | | | |
| ACT | GAT | CAA | AGA | TTT | AAT | GAC | ATT | CTT | CTG | CAG | CTA | AGT | ACC | TTG | TTT | 535 |
| Thr | Asp | Gln | Arg | Phe | Asn | Asp | Ile | Leu | Leu | Gln | Leu | Ser | Thr | Leu | Phe | |
| | | 150 | | | | | 155 | | | | | 160 | | | | |
| TCC | TCA | GTC | CAG | GGA | CAT | GGG | AAT | GCA | ATA | GAT | GAA | ATC | TCC | AAG | TCC | 583 |
| Ser | Ser | Val | Gln | Gly | His | Gly | Asn | Ala | Ile | Asp | Glu | Ile | Ser | Lys | Ser | |
| | 165 | | | | | 170 | | | | | 175 | | | | | |
| TTA | ATA | AGT | TTG | AAT | ACC | ACA | TTG | CTT | GAT | TTG | CAG | CTC | AAC | ATA | GAA | 631 |
| Leu | Ile | Ser | Leu | Asn | Thr | Thr | Leu | Leu | Asp | Leu | Gln | Leu | Asn | Ile | Glu | |
| 180 | | | | | 185 | | | | | 190 | | | | | 195 | |
| AAT | CTG | AAT | GGC | AAA | ATC | CAA | GAG | AAT | ACC | TTC | AAA | CAA | CAA | GAG | GAA | 679 |
| Asn | Leu | Asn | Gly | Lys | Ile | Gln | Glu | Asn | Thr | Phe | Lys | Gln | Gln | Glu | Glu | |
| | | | 200 | | | | | 205 | | | | | 210 | | | |
| ATC | AGT | AAA | TTA | GAG | GAG | CGT | GTT | TAC | AAT | GTA | TCA | GCA | GAA | ATT | ATG | 727 |
| Ile | Ser | Lys | Leu | Glu | Glu | Arg | Val | Tyr | Asn | Val | Ser | Ala | Glu | Ile | Met | |
| | | | 215 | | | | | 220 | | | | | 225 | | | |
| GCT | ATG | AAA | GAA | GAA | CAA | GTG | CAT | TTG | GAA | CAG | GAA | ATA | AAA | GGA | GAA | 775 |
| Ala | Met | Lys | Glu | Glu | Gln | Val | His | Leu | Glu | Gln | Glu | Ile | Lys | Gly | Glu | |
| | | 230 | | | | | 235 | | | | | 240 | | | | |
| GTG | AAA | GTA | CTG | AAT | AAC | ATC | ACT | AAT | GAT | CTC | AGA | CTG | AAA | GAT | TGG | 823 |
| Val | Lys | Val | Leu | Asn | Asn | Ile | Thr | Asn | Asp | Leu | Arg | Leu | Lys | Asp | Trp | |
| | 245 | | | | | 250 | | | | | 255 | | | | | |
| GAA | CAT | TCT | CAG | ACC | TTG | AGA | AAT | ATC | ACT | TTA | ATT | CAA | GGT | CCT | CCT | 871 |
| Glu | His | Ser | Gln | Thr | Leu | Arg | Asn | Ile | Thr | Leu | Ile | Gln | Gly | Pro | Pro | |
| 260 | | | | | 265 | | | | | 270 | | | | | 275 | |
| GGA | CCC | CCG | GGT | GAA | AAA | GGA | GAT | CGA | GGT | CCC | ACT | GGA | GAA | AGT | GGT | 919 |
| Gly | Pro | Pro | Gly | Glu | Lys | Gly | Asp | Arg | Gly | Pro | Thr | Gly | Glu | Ser | Gly | |
| | | | | 280 | | | | | 285 | | | | | 290 | | |
| CCA | CGA | GGA | TTT | CCA | GGT | CCA | ATA | GGT | CCT | CCG | GGT | CTT | AAA | GGT | GAT | 967 |
| Pro | Arg | Gly | Phe | Pro | Gly | Pro | Ile | Gly | Pro | Pro | Gly | Leu | Lys | Gly | Asp | |
| | | | 295 | | | | | 300 | | | | | 305 | | | |
| CGG | GGA | GCA | ATT | GGC | TTT | CCT | GGA | AGT | CGA | GGA | CTC | CCA | GGA | TAT | GCC | 1015 |
| Arg | Gly | Ala | Ile | Gly | Phe | Pro | Gly | Ser | Arg | Gly | Leu | Pro | Gly | Tyr | Ala | |
| | | | 310 | | | | | 315 | | | | | 320 | | | |
| GGA | AGG | CCA | GGA | AAT | TCT | GGA | CCA | AAA | GGC | CAG | AAA | GGG | GAA | AAG | GGG | 1063 |
| Gly | Arg | Pro | Gly | Asn | Ser | Gly | Pro | Lys | Gly | Gln | Lys | Gly | Glu | Lys | Gly | |
| | 325 | | | | | 330 | | | | | 335 | | | | | |
| AGT | GGA | AAC | ACA | TTA | ACT | CCA | TTT | ACG | AAA | GTT | CGA | CTG | GTC | GGT | GGG | 1111 |
| Ser | Gly | Asn | Thr | Leu | Thr | Pro | Phe | Thr | Lys | Val | Arg | Leu | Val | Gly | Gly | |
| 340 | | | | | 345 | | | | | 350 | | | | | 355 | |
| AGC | GGC | CCT | CAC | GAG | GGG | AGA | GTG | GAG | ATA | CTC | CAC | AGC | GGC | CAG | TGG | 1159 |
| Ser | Gly | Pro | His | Glu | Gly | Arg | Val | Glu | Ile | Leu | His | Ser | Gly | Gln | Trp | |
| | | | | 360 | | | | | 365 | | | | | 370 | | |
| GGT | ACA | ATT | TGT | GAC | GAT | CGC | TGG | GAA | GTG | CGC | GTT | GGA | CAG | GTC | GTC | 1207 |
| Gly | Thr | Ile | Cys | Asp | Asp | Arg | Trp | Glu | Val | Arg | Val | Gly | Gln | Val | Val | |
| | | | 375 | | | | | 380 | | | | | 385 | | | |
| TGT | AGG | AGC | TTG | GGA | TAC | CCA | GGT | GTT | CAA | GCC | GTG | CAC | AAG | GCA | GCT | 1255 |
| Cys | Arg | Ser | Leu | Gly | Tyr | Pro | Gly | Val | Gln | Ala | Val | His | Lys | Ala | Ala | |
| | | | 390 | | | | | 395 | | | | | 400 | | | |

```
CAC TTT GGA CAA GGT ACT GGT CCA ATA TGG CTG AAT GAA GTG TTT TGT    1303
His Phe Gly Gln Gly Thr Gly Pro Ile Trp Leu Asn Glu Val Phe Cys
    405             410             415

TTT GGG AGA GAA TCA TCT ATT GAA GAA TGT AAA ATT CGG CAA TGG GGG    1351
Phe Gly Arg Glu Ser Ser Ile Glu Glu Cys Lys Ile Arg Gln Trp Gly
420             425             430             435

ACA AGA GCC TGT TCA CAT TCT GAA GAT GCT GGA GTC ACT TGC ACT TTA    1399
Thr Arg Ala Cys Ser His Ser Glu Asp Ala Gly Val Thr Cys Thr Leu
            440             445             450

TAA TGCATCATAT TTTCATTCAC AACTATGAAA TCGCTGCTCA AAAATGATTT         1452
 *

TATTACCTTG TTCCTGTAAA ATCCATTTAA TCAATATTTA AGAGATTAAG AATATTGCCC  1512

AAATAATATT TTAGATTACA GGATTAATAT ATTGAACACC TTCATGCTTA CTATTTTATG  1572

TCTATATTTA AATCATTTTA ACTTCTATAG GTTTTAAAT GGAATTTTCT AATATAATGA   1632

CTTATATGCT GAATTGAACA TTTTGAAGTT TATAGCTTCC AGATTACAAA GGCCAAGGGT  1692

AATAGAAATG CATACCAGTA ATTGGCTCCA ATTCATAATA TGTTCACCAG GAGATTACAA  1752

TTTTTGCTC TTCTTGTCTT TGTAATCTAT TTAGTTGATT TTAATTACTT TCTGAATAAC   1812

GGAAGGGATC AGAAGATATC TTTTGTGCCT AGATTGCAAA ATCTCCAATC CACACATATT  1872

GTTTAAAAT AAGAATGTTA TCCAACTATT AAGATATCTC AATGTGCAAT AACTTGTGTA   1932

TTAGATATCA ATGTTAATGA TATGTCTTGG CCACTATGGA CCAGGGAGCT TATTTTCTT   1992

GTCATGTACT GACAACTGTT TAATTGAATC ATGAAG                            2028
```

(2) INFORMATION FOR SEQ ID NO:2:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Gln Trp Asp His Phe His Asn Gln Gln Glu Asp Thr Asp Ser
 1               5                  10                  15

Cys Ser Glu Ser Val Lys Phe Asp Ala Arg Ser Met Thr Ala Leu Leu
                20                  25                  30

Pro Pro Asn Pro Lys Asn Ser Pro Ser Leu Gln Glu Lys Leu Lys Ser
            35                  40                  45

Phe Lys Ala Ala Leu Ile Ala Leu Tyr Leu Leu Val Phe Ala Val Leu
    50                  55                  60

Ile Pro Leu Ile Gly Ile Val Ala Ala Gln Leu Leu Lys Trp Glu Thr
65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Glu Met Arg Phe Gln Glu
                100                 105                 110

Val Phe Met Glu His Met Ser Asn Met Glu Lys Arg Ile Gln His Ile
            115                 120                 125

Leu Asp Met Glu Ala Asn Leu Met Asp Thr Glu His Phe Gln Asn Phe
    130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175
```

```
Ser  Lys  Ser  Leu  Ile  Ser  Leu  Asn  Thr  Thr  Leu  Leu  Asp  Leu  Gln  Leu
               180                      185                    190

Asn  Ile  Glu  Asn  Leu  Asn  Gly  Lys  Ile  Gln  Glu  Asn  Thr  Phe  Lys  Gln
          195                      200                    205

Gln  Glu  Glu  Ile  Ser  Lys  Leu  Glu  Glu  Arg  Val  Tyr  Asn  Val  Ser  Ala
     210                      215                    220

Glu  Ile  Met  Ala  Met  Lys  Glu  Glu  Gln  Val  His  Leu  Glu  Gln  Glu  Ile
225                      230                    235                         240

Lys  Gly  Glu  Val  Lys  Val  Leu  Asn  Asn  Ile  Thr  Asn  Asp  Leu  Arg  Leu
                    245                      250                    255

Lys  Asp  Trp  Glu  His  Ser  Gln  Thr  Leu  Arg  Asn  Ile  Thr  Leu  Ile  Gln
               260                      265                    270

Gly  Pro  Pro  Gly  Pro  Pro  Gly  Glu  Lys  Gly  Asp  Arg  Gly  Pro  Thr  Gly
          275                      280                    285

Glu  Ser  Gly  Pro  Arg  Gly  Phe  Pro  Gly  Pro  Ile  Gly  Pro  Pro  Gly  Leu
     290                      295                    300

Lys  Gly  Asp  Arg  Gly  Ala  Ile  Gly  Phe  Pro  Gly  Ser  Arg  Gly  Leu  Pro
305                      310                    315                         320

Gly  Tyr  Ala  Gly  Arg  Pro  Gly  Asn  Ser  Gly  Pro  Lys  Gly  Gln  Lys  Gly
                    325                      330                    335

Glu  Lys  Gly  Ser  Gly  Asn  Thr  Leu  Thr  Pro  Phe  Thr  Lys  Val  Arg  Leu
               340                      345                    350

Val  Gly  Gly  Ser  Gly  Pro  His  Glu  Gly  Arg  Val  Glu  Ile  Leu  His  Ser
          355                      360                    365

Gly  Gln  Trp  Gly  Thr  Ile  Cys  Asp  Asp  Arg  Trp  Glu  Val  Arg  Val  Gly
     370                      375                    380

Gln  Val  Val  Cys  Arg  Ser  Leu  Gly  Tyr  Pro  Gly  Val  Gln  Ala  Val  His
385                      390                    395                         400

Lys  Ala  Ala  His  Phe  Gly  Gln  Gly  Thr  Gly  Pro  Ile  Trp  Leu  Asn  Glu
                    405                      410                    415

Val  Phe  Cys  Phe  Gly  Arg  Glu  Ser  Ser  Ile  Glu  Glu  Cys  Lys  Ile  Arg
               420                      425                    430

Gln  Trp  Gly  Thr  Arg  Ala  Cys  Ser  His  Ser  Glu  Asp  Ala  Gly  Val  Thr
          435                      440                    445

Cys  Thr  Leu
450
```

( 2 ) INFORMATION FOR SEQ ID NO:3:

( i ) SEQUENCE CHARACTERISTICS:
        ( A ) LENGTH: 1367 base pairs
        ( B ) TYPE: nucleic acid
        ( C ) STRANDEDNESS: double
        ( D ) TOPOLOGY: Not Relevant ( i i ) MOLECULE TYPE: cDNA to mRNA ( i x ) FEATURE:
        ( A ) NAME/KEY: CDS
        ( B ) LOCATION: 67..1143

( x i ) SEQUENCE DESCRIPTION: SEQ ID NO:3:

```
TAGGTTTCAA  TTGTAAAGAG  AGAGAAGTGG  ATAAATCAGT  GCTGCTTTCT  TTAGGACGAA            60

AGAAGT ATG GAG CAG TGG GAT CAC TTT CAC AAT CAA CAG GAG GAC ACT                   108
       Met Glu Gln Trp Asp His Phe His Asn Gln Gln Glu Asp Thr
       1               5                   10

GAT AGC TGC TCC GAA TCT GTG AAA TTT GAT GCT CGC TCA ATG ACA GCT                  156
Asp Ser Cys Ser Glu Ser Val Lys Phe Asp Ala Arg Ser Met Thr Ala
15              20                  25                  30
```

-continued

| | | | | | | | | | | | | | | | | |
|---|---|---|---|---|---|---|---|---|---|---|---|---|---|---|---|---|
| TTG | CTT | CCT | CCG | AAT | CCT | AAA | AAC | AGC | CCT | TCC | CTT | CAA | GAG | AAA | CTG | 204 |
| Leu | Leu | Pro | Pro | Asn 35 | Pro | Lys | Asn | Ser 40 | Pro | Ser | Leu | Gln | Glu | Lys 45 | Leu | |
| AAG | TCC | TTC | AAA | GCT | GCA | CTG | ATT | GCC | CTT | TAC | CTC | CTC | GTG | TTT | GCA | 252 |
| Lys | Ser | Phe | Lys 50 | Ala | Ala | Leu | Ile 55 | Ala | Leu | Tyr | Leu | Leu | Val 60 | Phe | Ala | |
| GTT | CTC | ATC | CCT | CTC | ATT | GGA | ATA | GTG | GCA | GCT | CAA | CTC | CTG | AAG | TGG | 300 |
| Val | Leu | Ile 65 | Pro | Leu | Ile | Gly | Ile 70 | Val | Ala | Ala | Gln | Leu 75 | Leu | Lys | Trp | |
| GAA | ACG | AAG | AAT | TGC | TCA | GTT | AGT | TCA | ACT | AAT | GCA | AAT | GAT | ATA | ACT | 348 |
| Glu | Thr 80 | Lys | Asn | Cys | Ser 85 | Val | Ser | Ser | Thr | Asn 90 | Ala | Asn | Asp | Ile | Thr | |
| CAA | AGT | CTC | ACG | GGA | AAA | GGA | AAT | GAC | AGC | GAA | GAG | GAA | ATG | AGA | TTT | 396 |
| Gln | Ser 95 | Leu | Thr | Gly | Lys | Gly 100 | Asn | Asp | Ser | Glu | Glu 105 | Glu | Met | Arg | Phe 110 | |
| CAA | GAA | GTC | TTT | ATG | GAA | CAC | ATG | AGC | AAC | ATG | GAG | AAG | AGA | ATC | CAG | 444 |
| Gln | Glu | Val | Phe | Met 115 | Glu | His | Met | Ser | Asn 120 | Met | Glu | Lys | Arg | Ile 125 | Gln | |
| CAT | ATT | TTA | GAC | ATG | GAA | GCC | AAC | CTC | ATG | GAC | ACA | GAG | CAT | TTC | CAA | 492 |
| His | Ile | Leu | Asp 130 | Met | Glu | Ala | Asn | Leu 135 | Met | Asp | Thr | Glu | His 140 | Phe | Gln | |
| AAT | TTC | AGC | ATG | ACA | ACT | GAT | CAA | AGA | TTT | AAT | GAC | ATT | CTT | CTG | CAG | 540 |
| Asn | Phe | Ser | Met 145 | Thr | Thr | Asp | Gln | Arg 150 | Phe | Asn | Asp | Ile | Leu 155 | Leu | Gln | |
| CTA | AGT | ACC | TTG | TTT | TCC | TCA | GTC | CAG | GGA | CAT | GGG | AAT | GCA | ATA | GAT | 588 |
| Leu | Ser 160 | Thr | Leu | Phe | Ser | Ser 165 | Val | Gln | Gly | His | Gly 170 | Asn | Ala | Ile | Asp | |
| GAA | ATC | TCC | AAG | TCC | TTA | ATA | AGT | TTG | AAT | ACC | ACA | TTG | CTT | GAT | TTG | 636 |
| Glu 175 | Ile | Ser | Lys | Ser | Leu 180 | Ile | Ser | Leu | Asn | Thr 185 | Thr | Leu | Leu | Asp | Leu 190 | |
| CAG | CTC | AAC | ATA | GAA | AAT | CTG | AAT | GGC | AAA | ATC | CAA | GAG | AAT | ACC | TTC | 684 |
| Gln | Leu | Asn | Ile | Glu 195 | Asn | Leu | Asn | Gly | Lys 200 | Ile | Gln | Glu | Asn | Thr 205 | Phe | |
| AAA | CAA | CAA | GAG | GAA | ATC | AGT | AAA | TTA | GAG | GAG | CGT | GTT | TAC | AAT | GTA | 732 |
| Lys | Gln | Gln | Glu 210 | Glu | Ile | Ser | Lys | Leu 215 | Glu | Glu | Arg | Val | Tyr 220 | Asn | Val | |
| TCA | GCA | GAA | ATT | ATG | GCT | ATG | AAA | GAA | GAA | CAA | GTG | CAT | TTG | GAA | CAG | 780 |
| Ser | Ala | Glu | Ile | Met 225 | Ala | Met | Lys | Glu | Glu 230 | Gln | Val | His | Leu | Glu 235 | Gln | |
| GAA | ATA | AAA | GGA | GAA | GTG | AAA | GTA | CTG | AAT | AAC | ATC | ACT | AAT | GAT | CTC | 828 |
| Glu | Ile | Lys | Gly 240 | Glu | Val | Lys | Val | Leu 245 | Asn | Asn | Ile | Thr | Asn 250 | Asp | Leu | |
| AGA | CTG | AAA | GAT | TGG | GAA | CAT | TCT | CAG | ACC | TTG | AGA | AAT | ATC | ACT | TTA | 876 |
| Arg 255 | Leu | Lys | Asp | Trp | Glu 260 | His | Ser | Gln | Thr | Leu 265 | Arg | Asn | Ile | Thr | Leu 270 | |
| ATT | CAA | GGT | CCT | CCT | GGA | CCC | CCG | GGT | GAA | AAA | GGA | GAT | CGA | GGT | CCC | 924 |
| Ile | Gln | Gly | Pro | Pro 275 | Gly | Pro | Pro | Gly | Glu 280 | Lys | Gly | Asp | Arg | Gly 285 | Pro | |
| ACT | GGA | GAA | AGT | GGT | CCA | CGA | GGA | TTT | CCA | GGT | CCA | ATA | GGT | CCT | CCG | 972 |
| Thr | Gly | Glu | Ser 290 | Gly | Pro | Arg | Gly | Phe 295 | Pro | Gly | Pro | Ile | Gly 300 | Pro | Pro | |
| GGT | CTT | AAA | GGT | GAT | CGG | GGA | GCA | ATT | GGC | TTT | CCT | GGA | AGT | CGA | GGA | 1020 |
| Gly | Leu | Lys 305 | Gly | Asp | Arg | Gly | Ala 310 | Ile | Gly | Phe | Pro | Gly 315 | Ser | Arg | Gly | |
| CTC | CCA | GGA | TAT | GCC | GGA | AGG | CCA | GGA | AAT | TCT | GGA | CCA | AAA | GGC | CAG | 1068 |
| Leu | Pro | Gly 320 | Tyr | Ala | Gly | Arg | Pro 325 | Gly | Asn | Ser | Gly | Pro 330 | Lys | Gly | Gln | |
| AAA | GGG | GAA | AAG | GGG | AGT | GGA | AAC | ACA | TTA | AGA | CCA | GTA | CAA | CTC | ACT | 1116 |
| Lys | Gly 335 | Glu | Lys | Gly | Ser | Gly 340 | Asn | Thr | Leu | Arg | Pro 345 | Val | Gln | Leu | Thr 350 | |

```
GAT CAT ATT AGG GCA GGG CCC TCT TAA GATCAGGTGG GTTGGGCGGG         1163
Asp His Ile Arg Ala Gly Pro Ser  *
                      355

ACATCCTCTG CTACCATCTC ATTAAAAGGC CCTTCACCTC TGGACAAGTC ATCTGCAACA 1223

ACTGACTTCC AAGATCCTTT TGTGACTCCT CCAAATGACT TTGGTTCCCG TGTTGTACCT 1283

GACTTCCACA TGGCCTTCTC TCCTGGTCCC TGGTGCTGTT TGGGCCTCTG CTCCCATGCT 1343

CATACCTCTT CTTACTCCAA TTAC                                        1367
```

(2) INFORMATION FOR SEQ ID NO:4:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Gln Trp Asp His Phe His Asn Gln Gln Glu Asp Thr Asp Ser
 1               5                  10                  15

Cys Ser Glu Ser Val Lys Phe Asp Ala Arg Ser Met Thr Ala Leu Leu
                20                  25                  30

Pro Pro Asn Pro Lys Asn Ser Pro Ser Leu Gln Glu Lys Leu Lys Ser
            35                  40                  45

Phe Lys Ala Ala Leu Ile Ala Leu Tyr Leu Leu Val Phe Ala Val Leu
 50                  55                  60

Ile Pro Leu Ile Gly Ile Val Ala Ala Gln Leu Leu Lys Trp Glu Thr
 65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Glu Met Arg Phe Gln Glu
                100                 105                 110

Val Phe Met Glu His Met Ser Asn Met Glu Lys Arg Ile Gln His Ile
                115                 120                 125

Leu Asp Met Glu Ala Asn Leu Met Asp Thr Glu His Phe Gln Asn Phe
    130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
                180                 185                 190

Asn Ile Glu Asn Leu Asn Gly Lys Ile Gln Glu Asn Thr Phe Lys Gln
    195                 200                 205

Gln Glu Glu Ile Ser Lys Leu Glu Glu Arg Val Tyr Asn Val Ser Ala
    210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
                260                 265                 270

Gly Pro Pro Gly Pro Pro Gly Glu Lys Gly Asp Arg Gly Pro Thr Gly
            275                 280                 285

Glu Ser Gly Pro Arg Gly Phe Pro Gly Pro Ile Gly Pro Pro Gly Leu
```

|  | 290 |  |  |  | 295 |  |  |  |  | 300 |  |  |  |  |
|---|---|---|---|---|---|---|---|---|---|---|---|---|---|---|
| Lys 305 | Gly | Asp | Arg | Gly | Ala 310 | Ile | Gly | Phe | Pro | Gly 315 | Ser | Arg | Gly | Leu | Pro 320 |
| Gly | Tyr | Ala | Gly | Arg 325 | Pro | Gly | Asn | Ser | Gly 330 | Pro | Lys | Gly | Gln | Lys 335 | Gly |
| Glu | Lys | Gly | Ser 340 | Gly | Asn | Thr | Leu | Arg 345 | Pro | Val | Gln | Leu | Thr 350 | Asp | His |
| Ile | Arg | Ala 355 | Gly | Pro | Ser |  |  |  |  |  |  |  |  |  |  |

ATTACHMENT ENHANCED 293 CELLS

FIELD OF THE INVENTION

This invention relates generally to cell lines used in the recombinant production, screening or measurement of protein or protein interactions in vitro.

BACKGROUND OF THE INVENTION

The primary human embryonic kidney (HEK) 293 cell line is a permanent line of cells transformed by sheared human adenovirus type 5 (Ad 5) DNA. The cells are particularly sensitive to human adenovirus, are highly permissive for adenovirus DNA, and contain and express the transforming genes of Ad5. This is a hypotriploid human cell line. See, F. Graham et al., *J. Gen. Virol.*, 36:59–72 (1977); T. Harrison et al., *Virology*, 77:319–329 (1977).

This cell line, which is readily available from commercial sources, such as the American Type Culture Collection, is used extensively in in vitro assays, and for the production of recombinant proteins and viruses. However, in washing steps which are conventionally and repeatedly employed in such in vitro assays and other manipulations of these cells, the cells readily detach or are washed away from the plates or dishes in which the studies are performed. This problem typically results in inaccurate, unreliably low measurement or collection of the protein, peptide or interaction to which the assay is directed.

There remains a need in the art for a cell substrate useful in in vitro manipulations in genetic engineering, which permits the measurement of accurate results.

BRIEF SUMMARY OF THE INVENTION

In one aspect, the invention provides improved HEK 293 cells, which cells are 293 cells which have been transfected with a mammalian macrophage scavenger receptor gene. Preferably, this gene is the human Type I or II macrophage scavenger receptor gene [SEQ ID NOS: 1 or 3].

In another aspect, the invention provides a method of enhancing the ability of HEK 293 cells to attach in tissue culture. This method involves the steps of transfecting 293 cells with a selected mammalian macrophage scavenger receptor gene.

In yet another aspect, the invention provides a method of screening compounds for biological activity which involves screening the improved 293 cells of the invention. In this method, the improved 293 cells have been further transfected with a selected gene and are then screened for expression of the selected gene. The cells expressing the selected genes are incubated in the presence of a compound of unknown biological activity, and then screened for the ability of the compound to affect the expressed gene product or its function.

Other aspects and advantages of the present invention are described further in the following detailed description of the preferred embodiments thereof.

BRIEF DESCRIPTION OF THE DRAWINGS

FIG. 1 provides the nucleic acid [SEQ ID NO:1] and amino acid [SEQ ID NO:2] sequences of the human macrophage scavenger receptor type I.

FIG. 2 provides the nucleic acid [SEQ ID NO:3] and amino acid [SEQ ID NO:4] sequences of the human macrophage scavenger receptor type II.

DETAILED DESCRIPTION OF THE INVENTION

The present invention provides an improved human embryonic kidney cell line, 293. The inventors have surprisingly found that human embryonic kidney (HEK) 293 cells transfected with a mammalian macrophage scavenger receptor gene demonstrate an enhanced ability to attach to a solid support as compared to conventional, unmodified 293 cells. In contrast to unmodified 293 cells, the improved 293 cells of the invention are not as readily washed away as unmodified 293 cells under the normal conditions of biological assays. Thus, the improved 293 cells of the invention are particularly well suited for use in in vitro studies and other applications for which unmodified 293 cells may be used.

As used herein "solid support" is any surface used for culturing, for in vitro assays, and the like. For example, a typical solid support is a plastic tissue culture plate, or a multi-well plate, hollow fibers, a test tube, conventionally employed plastic beads, glass beads, etc. Other solid supports are well known to those of skill in the art.

By "enhanced ability to attach" is meant that the transfected cells of this invention attach to the solid support with sufficient avidity to resist detachment which normally occurs with untransfected 293 cells caused by assay washing steps with buffer or growth medium. More specifically, the transfected cells of this invention because of the characteristic of enhanced attachment provide results of, for example, five times the cell number remaining after two washes as compared to the number of cells remaining following two washes of untransfected cells.

The human embryonic kidney cell line, 293, is readily available from the American Type Culture Collection, 12301 Parklawn Drive, Rockville, Md., U.S.A., under accession number ATCC CRL 1573. Also encompassed by this invention are progeny and derivatives of this cell line, which may be prepared using conventional techniques. See, Sambrook, *Molecular Cloning: A Laboratory Manual*, 2d ed., Cold Spring Harbor Press, Cold Spring Harbor, N.Y. (1989).

According to this invention, these cells are modified by transfection with a selected mammalian macrophage scavenger receptor (MSR) gene. Currently, in a preferred embodiment, this gene is selected from a human MSR Type I or Type II gene, and most preferably, the gene is characterized by the sequence provided in GenBank, under accession number D90187 (MSR Type I) or D90188 (MSR Type II). The sequences [SEQ ID NO:1 and 2] of MSR Type I are provided in FIG. 1. The sequences [SEQ ID NO: 3 and 4] of MSR Type II are provided in FIG. 2. Both of these genes were obtained from the human monocytic cell line THR-1 following four days of phorbol ester treatment. These two gene sequences are differential splice variants of a single human gene, and are described in more detail in A. Matsumoto et al., *Proc. Natl. Aced. Sci. USA*, 87:9133–9137 (1990), incorporated by reference herein.

It is anticipated that non-human homologs of MSR I or MSR II will be similarly useful in preparing the improved 293 cells according to the invention. Particularly desirable are the bovine [T. Kodama et al., *Proc. Natl. Aced. Sci. USA*, 85:9238–9242 (1988)], murine [M. Freeman et al., *Proc. Natl. Aced. Sci. USA*, 87:8810–8814 (1990)] and rabbit [P. E. Bickel and M. W. Freeman, *J. Clin. Invest.*, 90:1450–1457 (1992)] homologs, each of which is at least 60–80% homologous with the human MSR genes. It is further anticipated that other human scavenger receptor genes, particularly other genes which are produced recombinantly or are differentially selective for oxidized or acetylation-modified low density lipoprotein (LDL) species or another desired lipoprotein species, will be similarly useful.

One of these genes, preferably a human MSR gene, is selected and cloned into an appropriate vector for use in transfecting the 293 cells. Generally, a suitable expression vector is one which contains control or regulatory sequences operably linked with the nucleic acid sequences of the gene. These regulatory sequences are capable of directing the expression of the gene product in the 293 cells. Suitable vectors and regulatory sequences are well known to those of skill in the art and this invention is not limited by the selection thereof.

For example, suitable vectors may be, or contain components from, viral vectors selected from simian virus SV40, retroviruses, bovine papilloma virus, vaccinia virus, and adenovirus, or commonly used bacterial vectors or commonly used mammalian expression vectors or integrative vectors which lead to a stable expression cell line. The vector used in the examples below is pCDN [N. Aiyar et al., Mol. Cell. Biochem., 131:75–96 (1994)], which contains the promoter from cytomegalovirus, followed by a polycloning site and a polyadenylation site, the SV40 early enhancer, the human gene for dihydrofolate reductase, and a gene conferring resistance to neomycin.

Methods for introduction of a vector containing an MSR gene into mammalian cells are well known. Examples of suitable methods include, without limitation, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Sequences which contain selectable markers may also be transfected into the cell line. These markers may be contained on the vector containing the MSR gene, or may be separately transfected using conventional techniques, such as those described herein. Selectable markers for mammalian cells are known in the art, and include for example, thymidine kinase, dihydrofolate reductase (together with methotrexate as a DHFR amplifier), aminoglycoside phosphotransferase, hydromycin B phosphotransferase, asparagine synthetase, adenosine deaminase, metallothionien, and antibiotic resistant genes such as neomycin. Other markers may be readily selected by one of skill in the art, as desired.

As described in more detail below, if the MSR transfected cell is desired for use in a screening assay, the cell may also be transfected with other genes. The additional gene(s) may, for example, encode a protein which will be screened for biological activity or for interaction with the MSR or another transfected gene.

Following transfection with the selected MSR gene (and optionally, any other gene), the cells are incubated in a suitable selection medium, e.g., Eagles MEM, Dulbecco's MEM or the like.

Once modified to contain the MSR gene, or another suitable gene, according to the methods described above, the improved 293 cells are particularly well suited for use in any assay in which an unmodified 293 cell may be used. However the use of the improved 293 cells of the invention will result in superior attachment, and thus, more accurate test results.

An exemplary use of the improved 293 cells of the invention includes the use of these cells in a method of screening compounds for biological activity. This method involves the use of the attachment enhanced 293 cells of the invention which have been further transfected with a selected gene sequence. These cells are subsequently screened for expression of the selected gene. The cells expressing these selected genes are then incubated in the presence of a compound of unknown biological activity and further assayed for the ability of the compound to affect the expressed gene product.

Similarly, the attachment enhanced 293 cells of the invention may be used to identify antagonists of the MSR gene, i.e., to develop agents for atherosclerosis. Suitable assays for identifying antagonists to an expressed gene product are well known to those of skill in the art. See, T. Kodama et al., Nature, 343:531–535 (1990), A. M. Pearson et al., J. Biol. Chem., 268:3554 (1993).

The surprising result of enhanced attachment demonstrated by 293 cells transfected with MSR genes is not demonstrated when other cells, such as Chinese Hamster Ovary (CHO) cells, are transfected with MSR I or MSR II. To the inventors' knowledge, no other cell line has demonstrated this result when transfected with MSR genes.

The following examples illustrate the preferred methods for preparing the modified 293 cells of the invention and uses therefor. These examples are illustrative only and are not intended to limit the scope of the invention.

EXAMPLE 1

Calcium phosphate transfection of macrophage scavenger receptor I and II into human embryonic kidney 293 cells The macrophage scavenger receptor I or II cDNAs [SEQ ID NO:1 and 3, respectively] were subcloned into the mammalian expression vector pCDN in the correct orientation [N. Aiyar, Mol. Cell. Biochem., 131:75–86 (1994)].

The resulting construct containing the macrophage scavenger receptor I or II cDNA was used to transfect human embryonic kidney (HEK) 293 cells by calcium phosphate transfection. One day prior to the transfection, the HEK 293 cells were plated into 10 cm dishes at a density of $2 \times 10^5$ cells, so that the cells would be approximately 10% confluent within 24 hours. The cells were seeded into Eagle's Minimal Essential Medium (EMEM) supplemented with 2 mM L-glutamine and 10% fetal bovine serum (FBS).

The DNA was prepared for transfection by sterile ethanol precipitation. Following ethanol precipitation, the DNA pellet was dried inside a tissue culture hood. The pellet was then resuspended in 450 μL of sterile water and 50 μL of 2.5M $CaCl_2$. Ten μg of DNA were used per 10 cm dish. While gently swirling the DNA mixture, 500 μL of sterile 2×BBS (50 mM N,N-bis 2-hydroxyethyl-2-aminoethane sulfonic acid, 280 mM $NaCl_2$ and 1.5 mM $Na_2HPO_4$) was added. The BBS/DNA-$CaCl_2$ solution was allowed to form a precipitate by sitting at room temperature for 10–20 minutes.

The solution was then gently mixed to ensure adequate suspension of the precipitate and then added dropwise into the 10 cm dish of cells. The plate was gently swirled to distribute contents evenly. After a 12–16 hour incubation, the medium was carefully removed, and the cells were washed once with 5 ml of PBS (without $Ca^{2+}$ or $Mg^{2+}$) followed by the addition of 10 ml of EMEM supplemented with 2 mM L-glutamine and 10% FBS.

Following an overnight incubation, the medium was removed, and the cells were carefully washed once with 5 ml of PBS (without $Ca^{2+}$ or $Mg^{2+}$). To initiate selection, 10 ml of fresh EMEM with L-glutamine supplemented with 2 mM L-glutamine, 10% FBS and 0.4 mg/ml of geneticin (GIBCO-BRL) were added. Two or three days later, the medium was changed.

After approximately 2–3 weeks, each plate was examined under the microscope for small patches of growing cells. The patches were grown large enough to be seen as small spots on the bottom of the plate. Once at this stage, all of the medium was removed and 3 μL of trypsin was added directly to the patch of cells. By pipetting up and down several times, the patch of cells was transferred to a 24 well dish containing 1 ml of medium with geneticin. The cells were expanded from this 24 well stage to a 6 well plate or T-25 Flask. Because the 293 cells grow best in conditioned medium, cells were fed based on their rate of growth, but typically not more than once a week.

EXAMPLE 2

Comparison of transfected and untransfected 293 cells

To demonstrate the surprising results of the above transfection, and the greater accuracy obtained in using the transfected 293 cells in assays, transfected 293 cells of this invention and untransfected 293 cells were seeded at the same cell density (100,000 per well) into 24-well plastic tissue culture dishes. These cells were allowed to grow for two days before testing. Cell growth appeared to be equivalent.

The same biochemical assay was performed on the transfected and untransfected cells.

The presence of macrophage scavenger receptors was confirmed by incubating transfected 293 cells with $^{125}$[I]-acetylated LDL at a concentration of approximately 5 μg/ml (specific activity 100–300 cpm/ng protein) for 5 hours at 37° C., essentially as described in J. Ashkenas et al., *J. Lipid Res.*, 34:983–1000 (1993). In replicate experiments, $^{125}$[I]-acetylated LDL binding/uptake amounted to an average of 1.75 μg/mg protein (n=76). Where it has been possible to measure $^{125}$[I]-acetylated LDL binding/uptake to untransfected 293 cells, the average was 0.20 μg/mg protein (n=6). After the assays were performed on the cells, they were dissolved in 0.1M NaOH, and aliquots were used to determine total protein concentration by the Pierce BCA assay with bovine serum albumin as the standard. In an attempt to keep as many untransfected cells as possible attached to the culture dished, the untransfected cells were washed only twice, while the transfected cells were washed seven times as per the procedure cited above.

Superior attachment of the transfected cells was observed in a comparison of recoverable protein, with an average of 113±2.3 μg protein/well (n=24) versus the untransfected cells with an average of 21.8±4.8 μg protein/well (n=12).

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. Human embryonic kidney 293 cells transfected with mammalian macrophage scavenger receptor gene, said cells demonstrating an enhanced ability to attach to a solid support.

2. The cells according to claim 1 wherein said receptor gene is a human macrophage scavenger receptor gene Type I.

3. The cells according to claim 1 wherein the receptor gene is characterized by the sequence of GenBank accession number D90187 SEQ ID NO:1.

4. The cells according to claim 1 wherein said receptor gene is a human macrophage scavenger receptor gene Type II.

5. The cells according to claim 1 wherein the receptor gene is characterized by the sequence of GenBank accession number D90188 SEQ ID NO:2.

6. The cells according to claim 1 wherein said receptor gene is a macrophage scavenger receptor gene of a non-human species.

7. A solid support to which is attached human embryonic kidney 293 cells transfected with a mammalian scavenger receptor gene.

8. The support according to claim 7 wherein said receptor gene is a human macrophage scavenger receptor gene Type I.

9. The support according to claim 7 wherein the receptor gene is characterized by the sequence of GenBank accession number D90187 SEQ ID NO:1.

10. The support according to claim 7 wherein said receptor gene is a human macrophage scavenger receptor gene Type II.

11. The support according to claim 7 wherein the receptor gene is characterized by the sequence of GenBank accession number D90188 SEQ ID NO:2.

12. The support according to claim 7 wherein said receptor gene is a macrophage scavenger receptor gene of a non-human species.

* * * * *